United States Patent [19]
Griffith

[11] Patent Number: 6,073,050
[45] Date of Patent: Jun. 6, 2000

[54] EFFICIENT INTEGRATED RF TELEMETRY TRANSMITTER FOR USE WITH IMPLANTABLE DEVICE

[75] Inventor: Glen A. Griffith, Newbury Park, Calif.

[73] Assignee: Advanced Bionics Corporation, Sylmar, Calif.

[21] Appl. No.: 09/189,737

[22] Filed: Nov. 10, 1998

[51] Int. Cl.[7] .................................................. A61N 1/36
[52] U.S. Cl. ......................... 607/57; 607/60; 340/870.24
[58] Field of Search ................... 607/55, 56, 57, 607/60, 137, 154; 340/870.24, 870.19

[56] References Cited

U.S. PATENT DOCUMENTS

| | | | |
|---|---|---|---|
| 4,223,679 | 9/1980 | Schulman et al. | 128/419 |
| 4,267,410 | 5/1981 | Forster et al. | 180/107 |
| 4,428,377 | 1/1984 | Zollner et al. | 128/419 |
| 4,532,930 | 8/1985 | Crosby et al. | 128/419 |
| 4,592,359 | 6/1986 | Galbraith | 128/419 |
| 4,741,340 | 5/1988 | Batina et al. | 607/27 |
| 4,947,844 | 8/1990 | McDermott | 128/421 |
| 5,035,242 | 7/1991 | Franklin et al. | 607/108 |
| 5,279,292 | 1/1994 | Baumann et al. | 607/137 |
| 5,569,307 | 10/1996 | Schulman et al. | 607/56 |
| 5,584,869 | 12/1996 | Heck et al. | 607/57 |
| 5,690,693 | 11/1997 | Wang et al. | 607/61 |
| 5,715,837 | 2/1998 | Chen | 128/899 |
| 5,733,313 | 3/1998 | Barreras, Sr. et al. | 607/33 |
| 5,776,172 | 7/1998 | Schulman et al. | 607/56 |

*Primary Examiner*—Kennedy J. Schaetzle
*Attorney, Agent, or Firm*—Bryant R. Gold

[57] ABSTRACT

An efficient RF telemetry transmitter system includes a first stage and a second stage. The transmitter system sends power and data to an implant device using pulse-width modulation of a high fixed frequency clock signal, e.g., a 49 MHz clock signal, within the first stage in order to provide efficient generation of an RF output signal in the second stage. Digital logic gates and related circuitry, e.g., implemented in an application specific integrated circuit (ASIC), are used in the first stage to provide pulse-width modulation of the fixed frequency clock signal in order to optimally set the drive level of the output signal of the first stage, or inter-stage signal. ON/OFF keying, or other modulation scheme, further modulates the clock signal with data in the first stage. The second stage includes a Class-E amplifier circuit implemented with a single RF transistor, biased with a temperature-compensated offset voltage set just below the cut-off voltage of the transistor. An LC filter placed in the front end of the second stage filters out all but the fundamental frequency component of the inter-stage signal. The drive level of the inter-stage signal is selected to prevent both overdriving and underdriving of the Class-E amplifier. An adjustable or selectable collector voltage coupled to the single RF transistor allows the amplitude of the output signal to be set to an optimum power level for transmission to the implant device.

20 Claims, 6 Drawing Sheets

EFFICIENT INTEGRATED RF TELEMETRY TRANSMITTER FOR USE WITH IMPLANTABLE DEVICE

BACKGROUND OF THE INVENTION

The present invention relates to medical systems, and more particularly to a highly efficient integrated RF telemetry transmitter for efficiently communicating with and powering an implanted stimulator device, e.g., an implanted cochlear stimulator (ICS).

Implanted cochlear stimulator systems are known in the art. See, e.g., U.S. Pat. Nos. 4,267,410; 4,428,377; 4,532,930; 4,592,359; 4,947,844; and 5,569,307.

Any implantable medical device, including an ICS, requires operating power in order to perform its intended function. Most ICS devices receive operating power from an external control unit by way of an inductive or RF signal link. That is, the implanted unit includes a receiving coil. The external unit includes a transmission coil. During use of the system, the external transmission coil is positioned adjacent the implanted receiving coil and a high frequency carrier signal is applied to the external transmission coil. This carrier signal is coupled to the implanted receiving coil, even though there is no direct connection between the external and implanted coils, in much the same manner as an ac signal applied to a primary winding of a transformer is coupled to a secondary winding of the transformer, which secondary winding has no direct connection with the primary winding. Once received by the receiving coil, implanted circuitry rectifies the signal and converts it to a dc signal which is used as the operating power for the implant device. Moreover, modulation applied to the carrier signal provides a means for sending control signals to the implant device from the external device.

In recent years, a need and desire has arisen for the external unit of a medical system that controls and powers an implantable device, such as an ICS, to be smaller and lighter. In general, this means that the battery carried by the external unit, which powers both the external unit and the implant device, must also be smaller and lighter. In order to avoid the too frequent replacement and/or recharging of the battery carried by the external unit, and associated expense, this means that the operation of the circuits in both the external unit and implant device, as well as the transfer of power from the external unit to the implant device, must be made more efficient.

One of the circuit areas within the external unit that has heretofore proven to be relatively inefficient is the high frequency transmitter modulator. The high frequency transmitter modulator is the circuitry that allows a high frequency signal, e.g., the carrier signal, to be modulated with data prior to transmitting such signal to the receiving coil of the implant device. The design of such high frequency transmitter modulators has typically been founded on a sinusoidal design approach, used to make the actual transfer of signal energy from the external (transmitting) coil to the implant (receiving) coil more efficient. Disadvantageously, however, power amplifiers and other circuitry operating in a sinusoidal mode are notoriously inefficient from a power dissipation view point, and have traditionally required more components, and hence a larger size, than have other, e.g., digital and/or non-linear (non-sinusoidal) design approaches.

When the external unit has been realized in a large wearable unit that is carried on a belt or in a pocket of the user, connected by a long cable to a headpiece where the transmitting coil is housed, such inefficiency and larger size has been of little consequence. However, in order for a smaller external unit to be used, e.g., one that is worn behind the ear, such sinusoidal design approach, while theoretically effective at providing the desired function, results in less compact circuits that operate less efficiently than required. Thus, it is evident that there is a need for a high frequency transmitter modulator circuit that is both compact and efficient.

Coupled with the need for an efficient and compact high frequency transmitter modulator circuit is the need for an efficient and compact RF amplifier or driver circuit that receives the output signal from the transmitter modulator circuit and applies it to an antenna or transmitting coil for coupling to the implant device. Where the implant device also has the capability of sending telemetry signals back to the external unit ("back telemetry signals"), there is a similar need for a compact receiver circuit within the external unit to receive and process such back telemetry signals in an efficient, power-saving, manner.

SUMMARY OF THE INVENTION

The present invention addresses the above and other needs by providing an efficient RF telemetry transmitter system for sending power and data to an implant device. In one embodiment, the efficient RF telemetry transmitter described herein uses pulse-width modulation of a high frequency clock signal, e.g., a 49 MHz clock signal, within a first stage of a transmitter circuit in order to provide an efficient drive signal into a second stage transmitter circuit. The first stage transmitter circuit is preferably designed within an application specific integrated circuit (ASIC). The second stage transmitter circuit is preferably designed using efficiently-operated discrete circuitry, e.g., circuitry operating as a Class-E amplifier.

In accordance with one aspect of the present invention, a highly efficient integrated RF telemetry transmitter system is disclosed that is used within a behind-the-ear (BTE) unit of a cochlear stimulation system. Much of the circuitry included in such system is integrated directly onto a BTE ASIC that is mounted on a printed circuit board (PCB) housed within the BTE. Some of the circuits or elements of such system are implemented using discrete components which may also be mounted on the PCB. More particularly, in a preferred implementation, an oscillator circuit (OSC), transmitter modulator circuit (TX MOD), transmitter bias circuit (TX BIAS), and frequency modulated receiver circuit (FM RCVR) are all incorporated into a BTE ASIC; while a discrete crystal, transmitter amplifier circuit (TX AMP), and bandpass filter circuits (BPF) are implemented using discrete components. In such implementation (and using the terminology of the previous paragraph), it will be seen that the TX MOD operates as the first stage transmitter circuit, and the TX AMP operates as the second stage transmitter circuit.

Efficient operation of an implant device by an external unit requires that the transmitted RF signal sent to the implant device be adjustable in magnitude in order to assure optimum power transfer to the implant device. That is, the amount of power coupled into the implant device should be set to whatever level is demanded by the implant device, not more (which would mean power would be wasted), and not less (which means the implant device could not perform all of its intended functions). To this end, a power control loop may be established between the implant device and the BTE or other external unit, using back telemetry signals as feedback, to control the amount of power (e.g., control the amplitude) of the RF signal coupled into the implant device. While such a power control loop is not the subject, per se, of the present application (it is the subject of U.S. patent application Ser. No. 08/932,565, filed Sep. 19, 1997, assigned to the same assignee as is the present application, which application is incorporated herein by reference), the present invention may readily be used to aid in the implementation of such a power control loop, when used Efficient operation of the RF telemetry transmitter system of the present invention, when implemented using multiple stages, requires that the RF signal sent from one stage to another stage be adjustable, as required, so that the magnitude of the inter-stage signal may be set to the appropriate level for driving the next stage. That is, if the inter-stage signal is set or adjusted too low in magnitude, then the stage being driven by such signal will not operate as designed. Similarly, if the inter-stage signal is set or adjusted too high in magnitude, then the excess energy contained in such signal is wasted. That is to say, for efficient operation, the inter-stage signal must be set or adjusted so that it neither underdrives nor overdrives the subsequent stage. (Note, in this context, the term "magnitude" refers to the energy content of the signal, and may be adjusted by changing, e.g., the amplitude of the signal, the duty cycle [ratio of pulse width to pulse-repetition period] of the signal, the shape of the signal, or through other means.) Advantageously, the present invention provides a highly-efficient manner for making such adjustment of the inter-stage signal.

One aspect of the present invention is directed to a highly efficient, two stage, transmitter circuit that may be used within an external unit in order to efficiently produce and transmit a modulated RF power signal to an implant device. While such invention finds primary applicability in a cochlear stimulation system, e.g., a BTE cochlear stimulation system, it should be emphasized that such invention may also be used in any type of system wherein a high frequency RF signal must be generated and transmitted at minimal power consumption.

In accordance with another aspect of the invention, a high frequency carrier signal having an adjustable magnitude is generated through the use of an oscillator circuit, a transmitter modulator circuit, and an RF amplifier circuit. A fixed frequency carrier signal is first generated by the oscillator circuit and digital logic circuits. The transmitter modulator circuit then modulates the pulse width of the fixed frequency carrier signal to less than the nominal 50% duty cycle. Advantageously, such high frequency carrier signal generation and pulse width modulation (PWM) thereof is performed using highly efficient digital logic gates and circuitry. As explained below, the pulse width is modulated in order to efficiently produce an output signal having an adjustable magnitude (or adjustable drive level). Such output signal may then be applied as the input drive signal to a subsequent transmitter amplifier stage; or (in some embodiments) may be transmitted directly to a remote receiver as an RF output signal having a set power level associated therewith. The PWM signal thus produced may also be modulated with data using another modulation scheme, e.g., ON/OFF modulation.

In a preferred embodiment, the modulated carrier signal (modulated, e.g., with both pulse width modulation to control its energy content or drive level and ON/OFF keying to embed a data stream therein) is used as the inter-stage drive signal applied to the front end of an RF amplifier circuit. The front end of the RF amplifier circuit includes a band pass filter, or equivalent circuitry, that rejects the higher harmonics of the PWM carrier frequency, while passing the fundamental carrier frequency. The magnitude (or energy content or drive level) of the passed fundamental carrier frequency, however, varies as a function of the pulse width. Thus, the energy content (or drive level) can be set to a value that optimally drives the active element(s) of the RF amplifier circuit. Here, "optimally drives" means a signal which supplies sufficient energy for the amplifier to perform its intended amplification function, but does not supply (and thus does not waste) excess energy not needed by the amplifier to perform its amplification function. To reduce the magnitude (or energy content or drive level) of the carrier signal, the pulse width of the PWM carrier signal is made smaller (i.e., the duty cycle of the carrier signal is made lower). To increase the magnitude of the PWM carrier signal, the pulse width of the PWM carrier signal is made larger (i.e., the duty cycle of the carrier signal is made higher, but still $\leq 50\%$). Thus, in this manner, by adjusting the pulse width of the carrier signal, an inter-stage signal (or, in some embodiments, an RF output signal) is produced having an energy content or magnitude that is a function of the selected pulse width. In use, the energy of this inter-stage signal is selected or set, as required, so that the inter-stage signal optimally drives a second stage of the transmitter amplifier circuit, or (in some embodiments) drives an output antenna with an RF signal having a prescribed power level.

In accordance with yet a further aspect, an RF amplifier circuit used as the second stage of an RF transmitter amplifier made in accordance with the present invention includes a single RF transistor, and associated biasing and tuning elements, configured to operate as a Class-E amplifier. Advantageously, a Class-E amplifier operates in a switched mode (ON or OFF) which provides a very high collector efficiency that can theoretically approach 100%. In operation, the energy content, or drive level, of the inter-stage signal applied to such single RF transistor, in combination with a temperature-compensated bias circuit, is optimally set so that the single RF transistor is always sufficiently driven ON or OFF with each cycle of the inter-stage signal, but is not overdriven ON or OFF.

In one embodiment, the present invention may thus be characterized as an efficient, compact, high frequency RF telemetry circuit for use in a cochlear implant system. Such cochlear implant system includes an external part and an implant part. The implant part has an implantable receiver circuit and implantable means for generating and applying a stimulation current to a selected pair of implantable electrodes. The external part includes the RF telemetry transmitter, which transmitter is used for transmitting power and data to the implant part. The RF telemetry transmitter includes: (1) a fixed frequency oscillator that generates a fixed frequency clock signal; (2) a telemetry modulator circuit responsive to the fixed frequency clock signal and including a pulse width modulator for modulating the pulse width of the fixed frequency clock signal in accordance with a first modulation signal to produce an inter-stage drive signal; and (3) a telemetry amplifier circuit responsive to the inter-stage drive signal that efficiently produces an RF output signal at the fixed frequency of the clock signal for transmitting to the implantable receiver circuit of the implant part. Preferably, the telemetry amplifier circuit includes (a) a band pass filter circuit that rejects the higher harmonics of the inter-stage drive signal, while passing the fundamental frequency thereof, thereby causing the drive level of the passed fixed frequency clock signal to vary as a function of the selected first modulation signal, and (b) an output amplifier circuit that efficiently amplifies the inter-stage drive signal to produce an amplified fixed frequency RF output signal. The amplified fixed frequency RF output signal may then be transmitted to the receiver circuit through an antenna coil connected to the telemetry amplifier circuit.

In another embodiment, the invention may be further characterized as a method for efficiently transmitting a modulated carrier signal to an implanted remote receiver. Such method includes: (a) generating a fixed frequency clock signal having a frequency of F1 MHz, the clock signal comprising a train of pulses, each pulse having a pulse width, W, with the time interval between the leading edge of the adjacent pulses comprising a fixed time period T1 seconds, where T1=1/F1; (b) modulating the pulse width W of the first frequency clock signal in accordance with a selected first modulation signal to produce a pulse width modulated (PWM) inter-stage carrier signal, the first modulation signal defining the energy content, or drive level, of the PWM inter-stage carrier signal; (c) further modulating the PWM inter-stage carrier signal with data in accordance with a selected second modulation signal to produce a dual modulated inter-stage carrier signal, the second modulation signal representing data to be carried to the remote receiver via the modulated carrier signal; (d) applying the dual modulated inter-stage carrier signal to a band pass filter circuit that rejects the higher harmonics thereof, while passing the fundamental frequency of the fixed frequency clock signal, wherein the drive level of the passed fixed frequency clock signal varies as a function of the selected first modulation signal; (e) efficiently amplifying the passed fixed frequency clock signal to produce an RF output signal having a frequency of F1 MHz, the RF output signal having data embedded therein that varies as a function of the second modulation signal; and (f) transmitting the RF output signal to the remote receiver circuit through an antenna coil or equivalent.

An important feature of the invention is the manner in which the single RF transistor of the Class E amplifier is biased. A temperature compensated offset bias voltage is applied to the base of the single RF transistor used within the Class E amplifier that keeps the RF transistor turned off in the absence of the inter-stage drive signal, yet easily drives the RF transistor into saturation in the presence of the inter-stage drive signal. This feature, in combination with selecting the drive level of the inter-stage drive signal, allows the RF transistor to always be driven into saturation and cut-off without the need for being overdriven, and thus allows appreciably lower power input than might otherwise be required. This feature thus conserves operating power of the Class E amplifier circuit.

It is thus an object of the present invention to provide a compact, low power, highly efficient, RF telemetry transmitter circuit that may be used to transfer RF power from a limited power source, e.g., a small battery, through a barrier, such as the skin, to a device on the other side of the barrier, e.g., an implant device.

It is a further object of the invention, in one embodiment thereof, to provide a compact, low power, highly efficient, RF telemetry transmitter for use within a BTE unit of a cochlear implant system.

It is an additional object of the invention to provide a low power, highly efficient RF telemetry transmitter circuit wherein the drive level or energy content of a fixed frequency RF signal, which may comprise either an inter-stage signal or an RF output signal, may be controlled through pulse width modulation of a fixed frequency carrier input clock signal.

It is still another object of the invention to provide a highly compact and efficient RF telemetry transmitter circuit that operates at a fixed frequency, and wherein a clock signal generated by a single oscillator circuit may be shared for multiple functions. More particularly, in one embodiment, it is preferred that the single oscillator circuit generate both (1) an input signal for the telemetry transmitter circuit, and (2) a clock signal for other processing circuits within an application specific integrated circuit (ASIC) on which at least a first stage of the telemetry transmitter circuit is fabricated.

BRIEF DESCRIPTION OF THE DRAWINGS

The above and other aspects, objects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
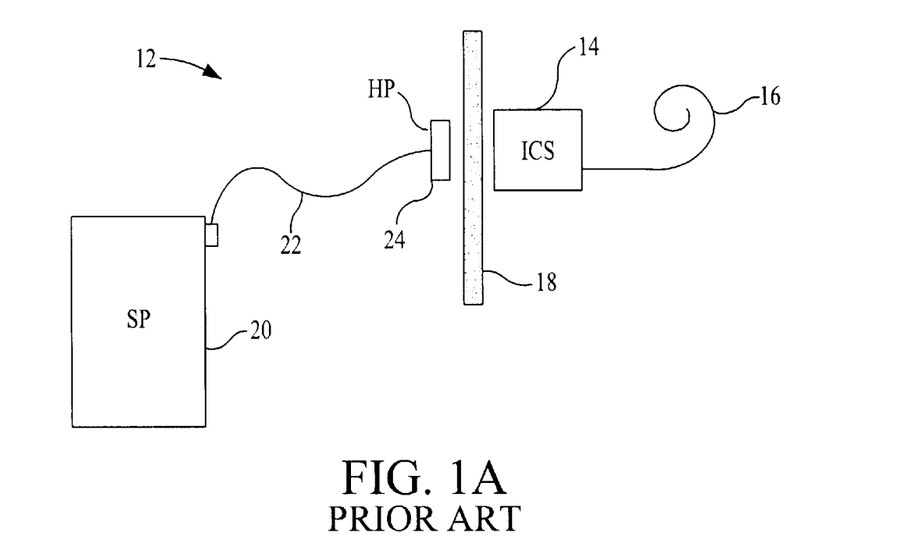
FIG. 1A shows a representative block diagram of an Implantable Cochlear Stimulation (ICS) system of the prior art.

Turning first to FIG. 1A, there is shown a representative block diagram of an Implantable Cochlear Stimulation (ICS)

system 12 of the type commonly found in the prior art. A thorough description of a cochlear stimulation system of the type shown in FIG. 1A may be found, e.g., in U.S. Pat. No. 5,776,172, incorporated herein by reference. As seen in FIG. 1A, the ICS system 12 includes an implanted portion, comprising an ICS 14 and an electrode array 16, and an external portion, comprising a speech processor (SP) 20 connected to a headpiece 24 via a long cable 22. The implanted portion is separated from the external portion by a barrier, e.g., a layer of skin 18.

Figure 1B:
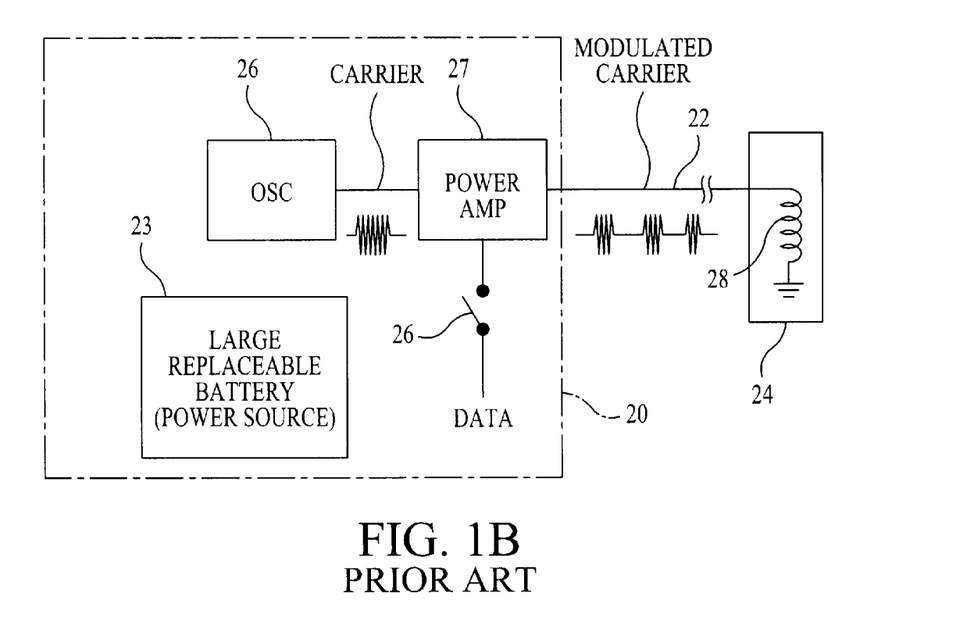
FIG. 1B shows a typical block diagram of a transmitter modulator used within the external speech processor (SP) of the ICS system of FIG. 1A.

In operation, the prior art ICS system 12 of FIG. 1A transmits power and data through the skin barrier 18 to the implantable portion using a technique as illustrated generally in the functional block diagram of FIG. 1B. The ICS system 12 uses the received data and power to provide stimulation pulses to select electrode pairs located along the electrode array 16, as is known in the art. The SP 20, as seen in FIG. 1B, includes an oscillator 26 that generates a carrier signal which is applied to a power amplifier 27. The power amplifier is modulated with data, e.g., through an ON/OFF modulation switch 29, and the resulting modulated amplified signal is sent to the headpiece 24 over the long cable 22, from which location it is transmitted to the implantable part through an antenna coil 28 housed within the headpiece 24.

Included within the SP 20 is a large replaceable battery 23, or other large power source. Such a large power source 23 is needed because the transmission scheme shown in FIG. 1B is not very efficient. That is, the power amplifier 27 is designed to amplify a sinusoidal signal, and as is readily known in the art, the amplification of sinusoidal signals is generally not an efficient process. This is because in order to amplify the sinusoidal signal without distortion, the various amplification stages, typically implemented using transistors, must operate in their linear (non-saturated) region. This means that significant amounts of power may be consumed, or lost, in the amplification stages as the amplification of the sinusoidal signal is carried out. While certain amplifier configurations may be selected in an attempt to make the sinusoidal amplification more efficient, e.g., the power amplifier 27 may be a Class C amplifier such amplifier configurations are still not all that efficient (a Class-C amplifier typically operates at about 55% collector efficiency) and require more components (and thus more space). Fortunately, for speech processor designs of the prior art, the efficiency and size of the SP 20 were not major design concerns because the SP is simply carried by the patient (thereby allowing it to be relatively large), and a large replaceable battery 23 housed within the SP 20 could simply be replaced, when needed. (Here, the term "sinusoidal" is used to refer to a sine wave signal having little or no distortion.)

It should be noted that having a sinusoidal signal to send to the antenna coil 28 in the headpiece 24 is generally viewed as good design practice. This is because the actual transmission or coupling of a modulated carrier signal to a receiver within the implanted ICS 14 functions best when the transmitted carrier signal comprises a sinusoidal signal. However, it is the generation of the sinusoidal carrier signal using amplifiers operating in their linear regions to amplify an input signal which is also essentially a sinusoidal signal that represents an inefficient process. This inefficient amplification process remains true, although to a lesser extent, even for design configurations, such as Class-C amplifiers, which operate in a switched mode. One of the advantages provided by the present invention, as explained more fully below, is that the amplification and modulation of the carrier signal does not require, at least in the initial stages, that the carrier signal be a sinusoidal signal which must be amplified using amplifiers operating in their linear regions. Hence, a significant power savings may be realized relative to the initial stages of the telemetry amplifier-/transmitter. It is only in the last stage of the amplifier/transmitter that the carrier signal need be converted to a sinusoidal signal, and such conversion is advantageously achieved by the present invention using a very efficient type of amplifier.

Figure 2:
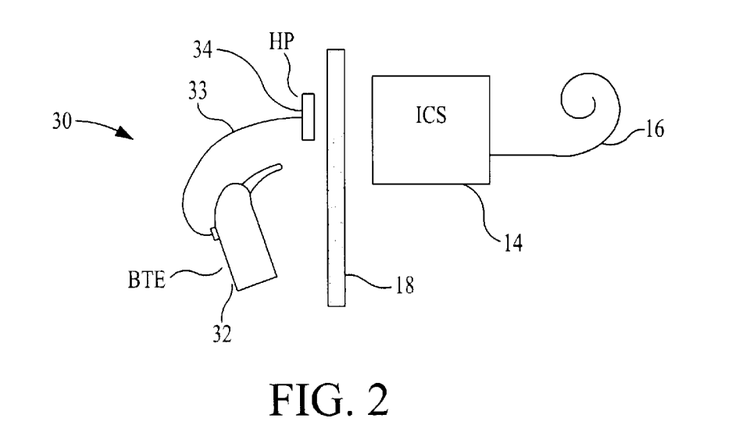
FIG. 2 illustrates the main components of a behind-the-ear (BTE) cochlear stimulation system of the type with which the present invention may be used.

Turning next to FIG. 2, there is shown the main components of a behind-the-ear (BTE) cochlear stimulation system 30 of the type with which the present invention may be used. The implanted portion of the system 30, i.e., the ICS 14 and electrode array 16, may be the same as have been used in prior art systems. The external portion of the system 30 comprises a BTE unit 32 coupled to a headpiece 34 via a short cable 33. A skin barrier 18 separates the external portion from the implanted portion. The BTE unit 32 houses a speech processor, a power source, the telemetry transmitter circuit of the present invention, as well as other standard components and speech processing circuits used within an ICS system.

The headpiece 34 houses an antenna coil, and may also house (in some embodiments) a microphone. In other embodiments, the microphone may be housed within or on the BTE unit 32. The BTE unit 32 is designed to be worn behind the ear of its user, and the headpiece 34 is connected thereto via the short (i.e., less than two inches or so) cable 33.

Because the BTE unit 32 shown in FIG. 2 is physically much smaller than is the SP unit 20 used with the prior ICS system 12 (FIG. 1A), and further because all of the circuits used within the BTE system 30 must perform substantially the same functions as are performed by equivalent circuits within the prior ICS system 12, it is necessary that such circuits perform their respective functions much more efficiently (i.e., by consuming less power than their prior art counterparts) because the power source used within the BTE system 30 cannot be as large, and hence cannot generally have the same capacity as, the power source used within the prior SP unit 20. While improved power sources (batteries) may be used in the BTE system 20 that provide a higher energy density, and hence more power in a smaller space or volume than has heretofore been achievable, it is still necessary that the circuits of the BTE system be designed with compactness and maximum efficiency in mind.

To that end, the present invention provides a highly efficient, compact, telemetry transmitter circuit for use in transmitting a modulated high frequency carrier signal across a barrier to a remote receiver, e.g., to an implanted receiver. Such an efficient, compact telemetry transmitter circuit, and related components, is illustrated in the block diagram shown in FIG. 3.

Figure 3:
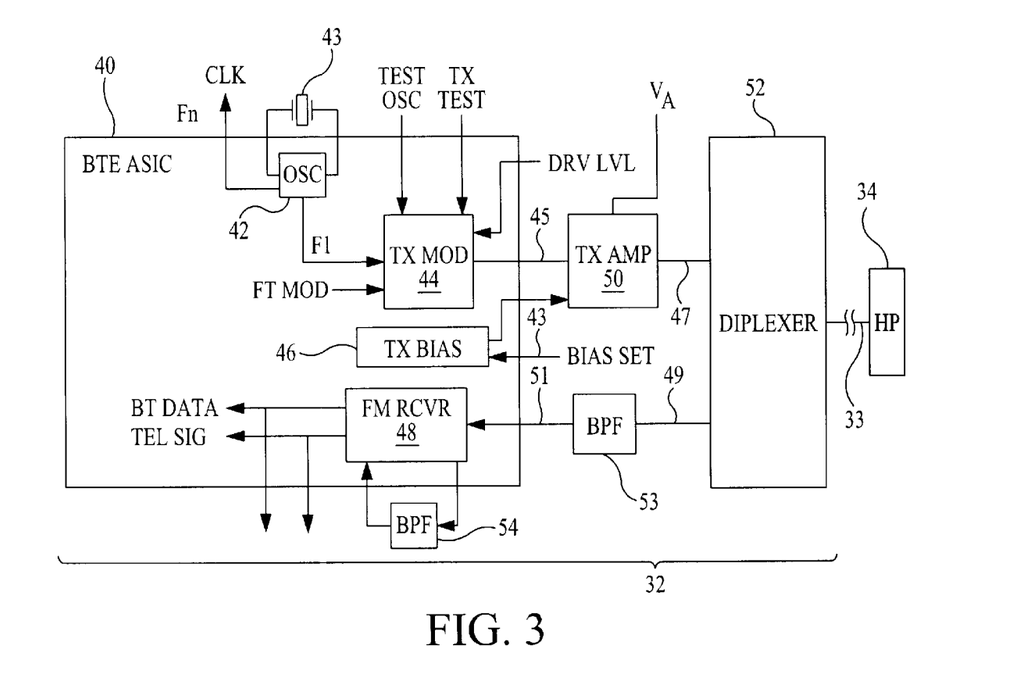
FIG. 3 is a block diagram of a transmitter modulator and related components in accordance with the present invention, which components, except for the headpiece (HP), are typically housed within the BTE unit of FIG. 2.

As seen in FIG. 3, the transmitter circuit includes an oscillator circuit (OSC) 42 that generates a primary clock signal having a frequency F1. In a preferred embodiment, the clock signal frequency F1 is 49 MHz. The OSC 42 may also generate other clock signals, e.g., a second clock signal Fn, having a frequency that is the same as or derived from the frequency F1 of the primary clock signal. For example, the second clock signal may have a frequency of 24.5 MHz, or ½ that of the primary clock signal.

The primary clock signal is applied to a telemetry modulator circuit (TX MOD) 44 where it is pulse-width modulated with a driver level (DRV LVL) signal and is also modulated with a data signal, referred to in the figures as the FT MOD signal. The resultant dual-modulated signal (modulated with both the DRV LVL and FT MOD signals), which may be referred to herein as an inter-stage signal, is then applied to a telemetry amplifier circuit (TX AMP) 50 over signal line 45. The TX AMP 50 derives its operating power from a supply voltage VA, which may be selected or adjusted, as required, to assume various values.

The TX AMP 50 efficiently amplifies the inter-stage signal received on signal line 45. As explained more fully below, such amplification is made more efficient by selecting the energy content (or drive level) of the inter-stage signal to be "just right", not too small (which would result in improper operation of the TX AMP 50), and not too large (which would result in the TX AMP 50 being overdriven, and would thus represent a waste of energy). The TX AMP 50, when optimally driven, operates efficiently to produce an RF output signal, on signal line 47, comprising a sinusoidal signal having an amplitude that varies as a function of the supply voltage, VA. Further, such RF output signal is modulated with data in a selected fashion as a function of the FT MOD signal. The RF output signal may then be applied, through a DIPLEXER circuit 52, to an antenna coil within the headpiece 34, where it is transmitted or coupled as a forward carrier signal, through the barrier 18 to the remote receiver.

A bias voltage generator circuit (TX BIAS) 46 is further included within the BTE unit 32. Such TX BIAS 46 creates an offset voltage for the TX AMP 50 which is just below the cut-in voltage of a transmitter amplifier transistor, as explained below. An external bias set resistor, connected to the TX BIAS 46 over signal line 43, allows variation or trimming of the offset voltage.

The headpiece 34 may also include an antenna coil tuned to receive a backtelemetry signal from the implanted receiver. In some embodiments, in order to simplify the design of the BTE unit 20, the back telemetry feature may be omitted. When used, such backtelemetry signal is modulated with data from the ICS 14, and is typically at a different carrier frequency than is the forward carrier signal transmitted to the implanted receiver. For example, in one embodiment, where the forward carrier signal operates at a fixed frequency of 49 MHz, the backtelemetry signal may have a fixed carrier frequency of 10.7 MHz. The type of modulation used to modulate the backtelemetry signal is preferably frequency modulation (FM), but other types of modulation could also be used.

The backtelemetry signal is separated in the DIPLEXER circuit 52 from the forward carrier signal and applied to a first bandpass filter circuit (BPF) 53 over signal line 49. The filtered backtelemetry signal is then directed, over signal path 51, to an FM receiver circuit (FM RCVR) 48. The FM RCVR 48 detects and demodulates the signal it receives over signal line 51. Typically, the FM RCVR 48 will utilize a second BPF 54 to aid in the detection and demodulation process. As a result of such demodulation, two signals are generated by the FM RCVR 48 and presented to the other circuits within the BTE unit 32. Such two other signals include a data signal (BT DATA) that represents the demodulated data received through the backtelemetry signal, and a signal (TEL SIG) that identifies the presence of a backtelemetry signal within the FM RCVR 48. The presence of the TEL SIG signal may thus be used to identify that a link has been established with the ICS 14. Knowing that a link has been established with an ICS may, in turn, be used for various purposes, see, e.g., U.S. Pat. No. 5,584,869, incorporated herein by reference.

It should be noted that, for some embodiments of the invention, the TX AMP 50 shown in FIG. 3 need not be used. In such instance, the inter-stage signal from the TX MOD 44, i.e., the signal on signal line 45, becomes the RF output signal and may be applied directly to the antenna coil in the headpiece 34. When this is done, several advantages are obtained. First, the power output of the RF signal may be controlled directly by the degree of pulse width modulation employed by the TX MOD 44, or equivalent pulse width modulation circuit. Thus, if an RF power transmit level of 1 mW is desired, then the width of the pulses within the signal on signal line 45 is appropriately adjusted so that the desired transmit level of 1 mW is obtained. Second, the amount of pulse width modulation applied to the carrier signal will translate into some amplitude modulation of the RF output signal. This amplitude modulation, which may be varied on a pulse-by-pulse basis, may be superimposed over the ON/OFF keying modulation of the data in order to effectively add an extra bit of information to each transmitted pulse, creating what may be termed a "di-bit". The use of a di-bits in this manner allows additional information to be transferred to the receiver of the implant device, thereby increasing the information transfer rate to the implant device.

Turning again to FIG. 3, it is seen that all of the components used within the telemetry transmitter circuit, with the exception of the headpiece 34, may be housed within the BTE unit 32. Further, the OSC 42, TX MOD 44, TX BIAS 46 and FM RCVR 48 (when used) may all preferably be formed or embedded within the same application specific integrated circuit (ASIC) 40. Such ASIC 40 may also include the other digital circuits associated with the BTE unit 22, such as the speech processing circuits, and hence the ASIC 40 may be referred to as the BTE ASIC. The BTE ASIC 40 is mounted on a suitable pc board (PCB) within the BTE unit 32. Other discrete components, not part of the ASIC 40, are then mounted, as required, on the BTE PCB or otherwise housed within the BTE unit. Such other discrete components may include, in addition to the battery (not shown in FIG. 3), e.g., a crystal 43 used with the OSC 42 to precisely control the frequency F1 of the OSC 42, the TX AMP 50, the DIPLEXER 52, and the first BPF 53 and the second BPF 54.

Figure 4:
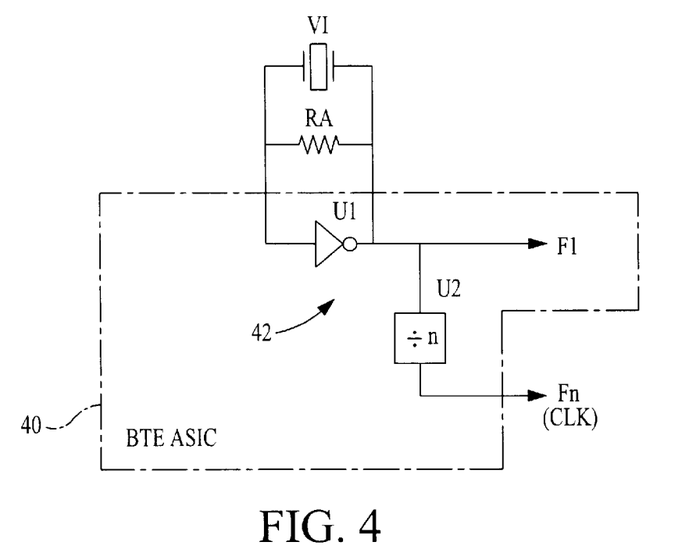
FIG. 4 depicts one implementation of the oscillator (OSC) circuit of FIG. 3.

FIG. 4 depicts one implementation of the oscillator (OSC) circuit 42 of FIG. 3. The oscillator circuit, which in a preferred embodiment comprises a 49 MHz oscillator, is a fundamental mode gate-oscillator. It is fabricated by connecting a crystal Y1 between the input and output pins of a CMOS inverter gate U1. A bias resistor RA parallels the crystal Y1, and load capacitors (not shown) may be attached to both the input and output pins of the inverter U1, as required. The output clock signal, of frequency F1, (and referred to herein as the clock signal F1) is provided at the output pin of the inverter U1. A divide by n circuit U2, where n is an integer, may further divide the output clock signal F1 by an appropriate factor to provide a secondary clock signal Fn. The divide by n circuit U2, where n is two, may be realized using a single CMOS J-K flip flop configured in the toggle-mode. The secondary clock signal may be used, e.g., for the digital signal processing (DSP) circuits of the BTE unit 32. In this manner, a single OSC 42 generates all of the clock signals needed within the BTE, as well as the telemetry transmitter, and the need for additional oscillator circuits is avoided.

Figure 5:
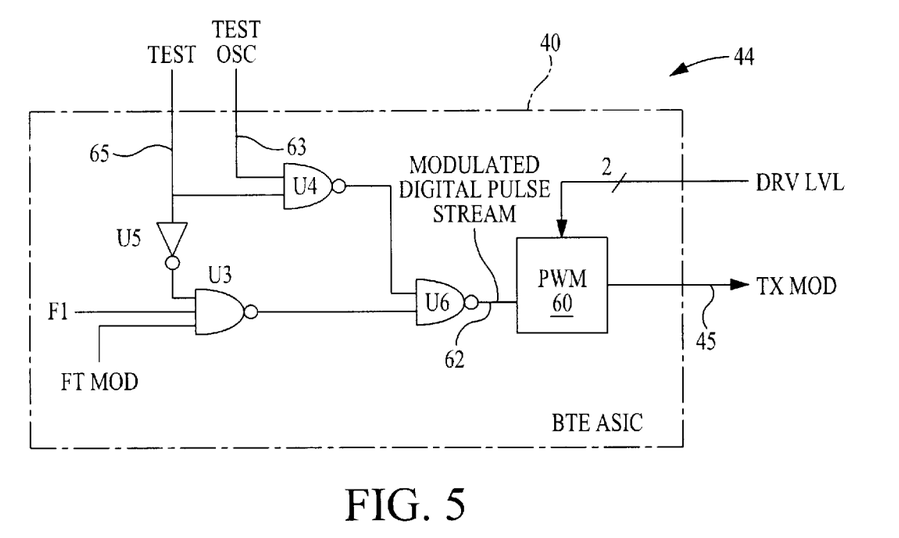
FIG. 5 illustrates one implementation of the transmitter modulator (TX MOD) circuit of FIG. 3.

FIG. 5 illustrates one implementation of the transmitter modulator circuit (TX MOD) 44 of FIG. 3. As seen in FIG. 5, the TX MOD 44 combines the FT MOD data stream (the data used to modulate the carrier) with the clock signal F1 in AND gate U3. Where the clock signal F1 comprises a 49

MHz clock, this produces a stream of 49 MHz pulses on signal line 62 which may then be ON/OFF modulated into Manchester-type 1.2 MBaud data pulses. A 2-to-1 multiplexer, realized using gates U5, U4 and U6, may be used to allow selection of either the normal 49 MHz source, i.e., the clock signal F1, or an external test oscillator (TEST OSC) clock signal, at signal line 63. A TEST signal, on line 65, is pulled HIGH to select the TEST OSC signal, and LOW for normal (selection of the clock signal F1) operation.

Still referring to FIG. 5, the modulated digital pulse stream is passed through a Pulse Width Modulator (PWM) circuit 60. In a preferred embodiment, the PWM 60 reduces the pulse width of the nominally 50% duty cycle modulated clock signal F1 to 1-of-4 preselected levels set by the 2-bit input of the signal DRV LVL. Such pulse width modulation may be achieved by selecting the charge/discharge current generator rates which feed a small integrated capacitor. This creates a variable time delay through the logic switching that shortens the width of the pulse.

It should be noted that any pulse width modulation technique could, of course, also be used to set the pulse width of the modulated clock signal F1 to 1-of-4 preselected levels. Alternatively, the pulse width may be set to 1-of-n discrete levels, where n is an integer that may assume any value, e.g., of from 2 to 16, or to any value. As should be evident from the descriptions presented herein, it is in part the use of the PWM 60 that allows the telemetry modulator circuit 44 to operate in an efficient manner, e.g., by passing and processing only digital pulses, not sinusoidal waveforms. This is because the circuitry (logic gates, transistor switches, etc.) through which the digital pulses must pass as they are processed within the TX MOD 44 may always be either ON or OFF, thereby significantly reducing the amount of power that is dissipated in such circuitry. Yet, by varying the pulse width in the manner described herein, and through the use of a TX AMP 50 as described herein, an output sinusoidal signal may ultimately be obtained at very low power cost for transmission to a remote receiver.

As explained in more detail below in connection with FIG. 8, the output of the PWM 60 (which comprises a modulated data pulse stream, where the data pulses have been shortened as explained above), on signal line 45, is fed to a resonant F1 bandpass filter, e.g., a 49 MHz resonant bandpass filter, located in the front end of the TX AMP 50. This resonant bandpass filter passes a sinusoidal voltage waveform at frequency F1, the drive level of which is proportional to the pulse width of the pulses contained within the modulated pulse stream, or inter-stage signal, on signal line 45. This technique of creating a sinusoidal signal at frequency F1, having a selectable drive level, advantageously allows a reduction in input power supplied to the input of the TX AMP 50, as well as a reduction in the power dissipated in the BTE ASIC output circuit. That is, as explained in more detail below in conjunction with the description of FIGS. 7 and 8, the selectable drive level of the signal that is applied to the input of the TX AMP 50 allows such drive level to be optimally selected for a drive that is not too weak, and not too strong.

Figure 6A:
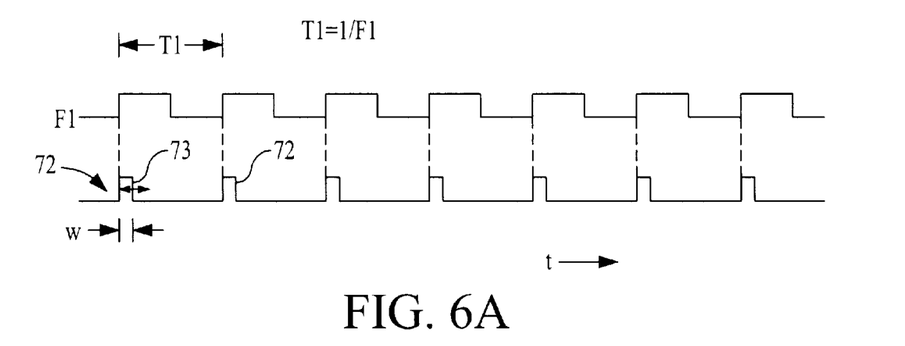
FIG. 6A illustrates one manner in which the pulse width modulator (PWM) circuit of FIG. 5 may modulate the pulse width of the carrier signal, providing a carrier signal having a pulse width that may assume any selected width.
Figure 6B:
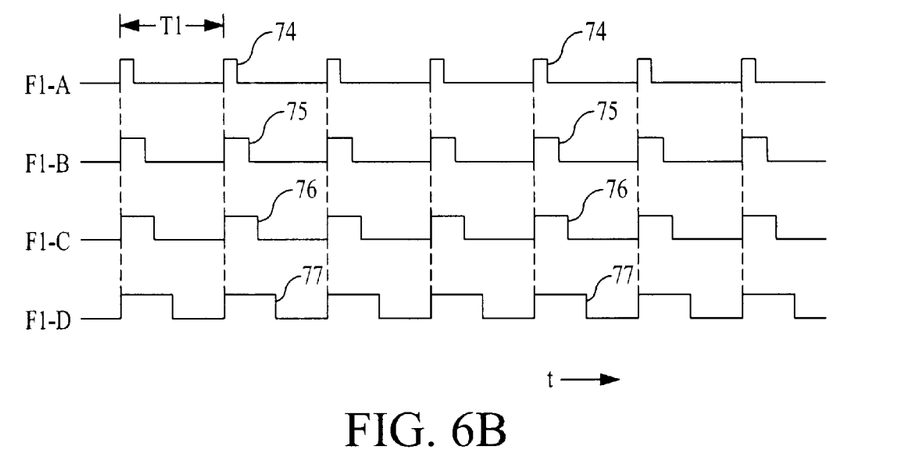
FIG. 6B illustrates another manner in which the PWM circuit of FIG. 5 may modulate the pulse width of the carrier signal, providing a carrier signal having a discrete number of pulse widths, e.g., four pulse widths, any one of which may be selected.
Figure 6C:
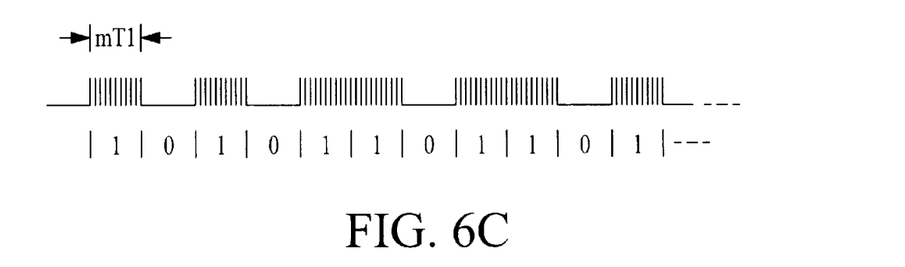
FIG. 6C illustrates one manner in which the carrier signal may be modulated with digital data, providing bit periods wherein the carrier signal is present or not present.

To further understand the manner in which the telemetry modulator circuit 44 operates, reference is made to the timing waveform diagrams shown in FIGS. 6A, 6B and 6C. FIG. 6A, for example, illustrates one manner in which the pulse width modulator (PWM) circuit 44 may operate. In FIG. 6A, the top waveform represents the clock signal F1, having a cycle period of T1. Note that the frequency F1 is the inverse of the period T1. Thus, if F1 were 50 MHz, then T1 would be ⅟50 MHz=0.020 $\mu$sec, or 20 nanoseconds. Where F1 is 49 MHz, then T1 would be about 20.4 nanoseconds. In FIG. 6A, the clock signal F1 is modulated so that the pulse width (W) of each pulse 72 in the output signal, the lower waveform, may assume any desired value, as represented by the double-headed arrow on the trailing edge 73 of the pulse 72. However, even though the width of the individual pulses may vary, the time interval between the leading edge of successive pulses 72 does not change. It remains as the time interval T1, which means the pulse repetition rate associated with the pulse stream remains at frequency F1.

FIG. 6B illustrates the preferred manner in which the PWM 44 modulates the pulse width of the carrier clock signal F1. As seen in FIG. 6B, one-of-four possible pulse widths are provided. These four possible pulse widths are represented in the four possible output pulse streams shown in FIG. 6B. A selected one of these four possible pulse streams is passed to the telemetry amplifier circuit (TX AMP) 50. A first pulse stream, F1-A, has a frequency of F1 and a first narrow pulse width, e.g., so that the pulse stream exhibits a duty cycle of about 6.25%. A second pulse stream, F1-B, also has a frequency of F1, but has a pulse width that is somewhat wider, e.g., so as to exhibit a duty cycle of about 12.5%. A third pulse stream, F1-C, likewise has a frequency of F1, but has a pulse width that is wider still, exhibiting a duty cycle of about 25%. A fourth pulse stream, F1-D, has a pulse width that is approximately 50% of the cycle period T1, thereby exhibiting a duty cycle of about 50%. These four duty cycles, represented in the waveforms F1-A, F1-B, F1-C and F1-D, are only exemplary. Other duty cycles could also be used, e.g., duty cycles of 20%, 30%, 40% and 50%, respectively. In operation, one of the F1-A, F1-B, F1-C, or F1-D pulse streams is selected by the 2-bit DRV LVL signal.

FIG. 6C depicts one manner in which the carrier clock signal F1 may be modulated with digital data using ON/OFF keying. In accordance with such modulation scheme, a stream of bit periods, of mT1 seconds each, are provided in which the carrier signal data pulses are present or not present, where m is the number of data pulses included in each bit period, and the time interval between successive data pulses is T1 seconds. Thus, for example, if T1 is equal to 20 nanoseconds, and m is equal to 10, then each bit period is 10×20=200 nanoseconds, or 0.20 $\mu$sec (where "$\mu$sec" stands for microseconds). The data scheme shown in FIG. 6C assumes that a digital "1" is represented by the presence of a burst of pulses during the data bit time, and that a digital "0" is represented by the absence of a burst of pulses during the data bit time. (This assignment, of course, could just as easily be reversed, with a digital "0" being represented by the presence of the data pulses, and a digital "1" being represented by the absence of the data pulses.) Thus, the data stream shown in FIG. 6C is representative of a digital data sequence:

"10101101101 . . . ."

Such a digital data sequence may, in turn, be encoded using a suitable encoding scheme, as is known in the art, e.g., a Manchester-type encoding scheme, to create a sequence of digital data words at a desired Baud rate.

Figure 7:
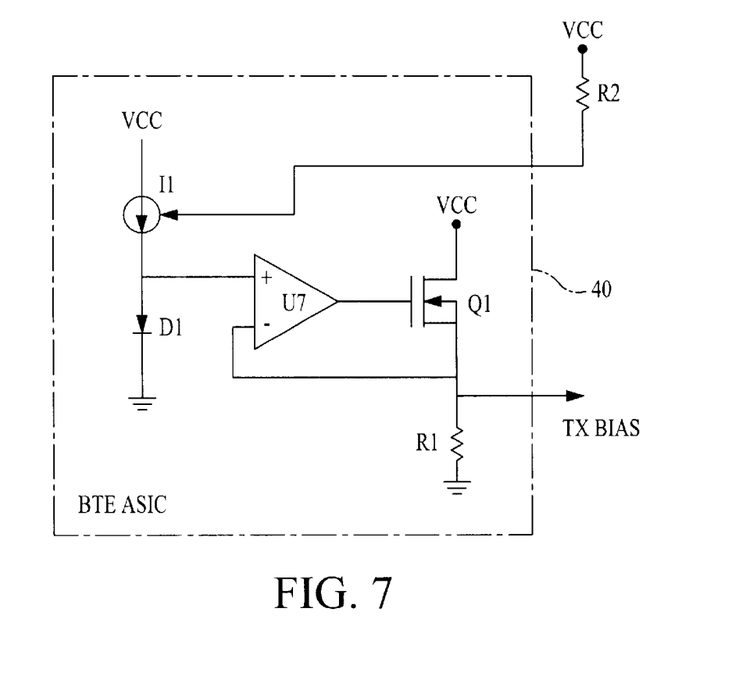
FIG. 7 shows one implementation of the transmitter bias (TX BIAS) circuit of FIG. 3.

Turning next to FIG. 7, the transmitter bias circuit (TX BIAS) 46 is illustrated. It is the function of the TX BIAS 46 to develop an offset voltage which is temperature compensated to approximate the base-emitter voltage of the RF transistor used in the transmitter amplifier circuit (TX AMP) 50, described below (FIG. 8). The addition of an offset voltage to the RF transistor allows it to be driven into saturation and cut-off with an appreciably lower level power input, hence providing a power savings feature. As seen in FIG. 7, a current generator I1 provides a constant current to a diode junction D1. A buffer-follower amplifier U7 and a driver transistor Q1 provide a constant voltage output, identified as "TX BIAS". An internal load resistor R1 ensures that some load current is present to keep the output transistor Q1 in its active region. An external current setting resistor R2 is used for trimming or modification of the current generator current setting.

The bias voltage level of the signal TX BIAS is chosen to ensure that the RF transistor Q2 (discussed in connection with FIG. 8, below), is just below cut-in. The added RF drive then causes the RF transistor to alternatively be driven from cut-off to saturation with very little signal swing.

It is noted that the optimum location for the temperature compensating diode D1 is within, or mounted on, the flange of the RF transistor Q2. (In this regard, it should be noted that D1 could be realized from the base-emitter junction of another transistor matched to transistor Q2, which other transistor may even be housed in the same package, on the same substrate, as transistor Q2.) If this cannot be done, then the diode D1 may be placed on or embedded within or near the ASIC 40, yielding a greater margin in the bias voltage range due to the slight temperature difference of the TX BIAS 46 and the TX AMP transistor Q2.

Figure 8:
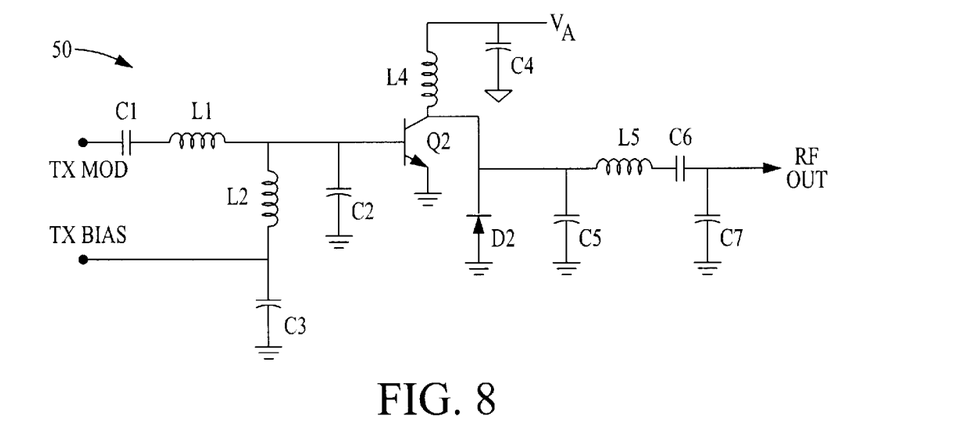
FIG. 8 depicts a preferred implementation of the transmitter amplifier (TX AMP) circuit of FIG. 3.

Turning next to FIG. 8, there is shown a preferred implementation of the transmitter amplifier circuit (TX AMP) 50 of FIG. 3. The TX AMP 50 includes a single RF transistor Q2, biased with the TX BIAS signal to be just below its cut-in point, configured to operate as a Class E amplifier. Advantageously, Class-E operation provides very high collector efficiencies and RF amplification which can theoretically approach 100%. In practice, the measured efficiency of the Class-E amplifier may range from 75–85% or higher. Such efficiency provides a significant improvement over the typical 55% efficiency achieved using a Class-C amplifier, as is commonly done in the prior art. The RF transistor Q2 has an input impedance characteristic of an RF switch at the power levels of interest. That is, when ON, the impedance of Q2 approaches that of a closed switch (very low impedance), and when OFF, the impedance of Q2 approaches that of an open switch (very high impedance).

Class-E operation is a switch-mode operation wherein the transistor Q2 commutates the collector circuit between the applied collector voltage, VA, and ground. An LC network, including inductor L5 and capacitor C5, is chosen for the desired load resistance to ring the collector voltage in such a way that the voltage across transistor Q2, and the rate of change of such voltage, dv/dt, are zero at the time the transistor begins conduction. Thus, power dissipation in Q2 is minimized, since it always has either zero volts, or zero current across it when it switches. While transistor Q2 is depicted as an NPN transistor, it is noted that an equivalent Class-E configuration could readily be implemented by those of skill in the art using a PNP transistor or other types of transistors and switching devices, e.g., MOSFET, GaAsFET, logic gates, and the like.

An input LC network of the TX AMP 50 is included in the front end of the circuitry shown in FIG. 8. Such input LC network includes capacitors C1, C2 and C3, and inductors L1 and L2. This LC network serves three main functions: (1) it provides a dc-bias path to the base of the RF transistor Q2; (2) it provides a bandpass filter action which rejects the higher harmonics of the carrier frequency F1 while passing the fundamental carrier frequency F1; and (3) it provides an impedance matching action which sets the power level transferred into the base circuit of the RF transistor Q2. More particularly, as seen in FIG. 8, capacitor C1 and inductor L1 are series tuned to pass the F1 carrier frequency, and provide a high impedance to all the higher harmonics. Although it would be possible to directly drive the transistor with conventional RC-pulse transistor coupling, such method dissipates the charge stored in the coupling capacitor, and the base capacitances during every cycle. The input LC network of FIG. 8, in contrast, which is resonant with the frequency F1, allows the charge stored in the coupling capacitors to be retained in the resonating inductors, thereby making the circuit more efficient.

Still with reference to FIG. 8, in order to minimize the effects of the inherent transistor collector-base capacitance of transistor Q2, the input is loaded with a large capacitance C2. This increases the Q of the network, and as described tends to swamp out the Miller feedback effects of the collector.

At the base of Q2, the base-emitter junction functions as a diode rectifier, and passes current through the junction only during the forward cycles, and is cut-off during the reverse portion of the cycle. This results in power dissipation in the base only during the conduction period of the junction. During the remaining portion of the RF cycle, the charge oscillates between the capacitors and the inductors.

The net current flow in the base circuit is provided by the offset bias generator, i.e., the TX BIAS 46. The source resistance of the bias generator must be low enough so that appreciable voltage drop does not occur and change the bias conduction. As described previously, the bias voltage provided by the TX BIAS 46 is temperature compensated so as to track temperature changes that occur in the base-emitter voltage of transistor Q2.

It should be noted that the power transferred to the base of transistor Q2 is determined, in part, by the resistance of the logic gate driver (located in the output stage of the PWM 60 of the TX MOD 44), the voltage of the logic gate driver, the input resistance of transistor Q2, and the degree of pulse width modulation (drive level) of the input signal. Characterization of different logic families that may be used in the TX MOD 44 show that an output resistance of about 30 Ohms is typical of several CMOS FPGA devices, and the AC-logic family. The transistor resistance of Q2 is typically near 50-Ohms. The maximum available power as determined by the logic gate voltage (e.g., 2 volts), and an output resistance of 30-Ohms, is thus about 6.8 mW. The inherent mismatch of the resistance can be used to reduce the power level to about 4.2 mW. A power level between 1–4 mW is appropriate to drive the biased transistor Q2. Further reduction in the logic gate power can be attained by the pulse width modulation of the TX MOD 44.

Still with reference to FIG. 8, the capacitor C3 should be selected to be sufficiently large so as to afford a low impedance at the carrier frequency F1, as well as frequencies far below the carrier frequency F1. This will thus significantly reduce the gain of the amplifier for frequency components that are out-of-band.

The collector circuit of transistor Q2 includes inductor L4 that connects the collector of Q2 to the amplifier supply voltage VA. Capacitor C4 is also tied to VA. L4 and C4 thus function as an AC-blocking circuit that allows DC-current to flow to the amplifier, but prevents AC-current flow from passing to the power supply. The capacitor C5 adds to the transistor parasitic collector-emitter capacitance, and is a part of the network with inductor L5 and capacitor C6 to cause the desired collector waveform (sinusoidal). Inductor L5 and capacitor C7 further form an impedance transforming network which matches the collector circuit of Q2 to the load resistance. Diode D2 is a flyback catch-diode that prevents excess reverse collector current flow for a mismatched load condition when the collector voltage may ring below ground. Such current bypassing also reduces disruption of the base bias circuit through the collector-base capacitance.

It is a feature of the present invention that the amplifier supply voltage VA may be adjusted, as required, in order to adjust or optimize the output level of the transmitted RF output signal. More particularly, the transmitter amplifier supply voltage VA may be selected to be whatever voltage is needed or desired for powering the implant or remote device. Typically, VA will be selectable from approximately 2 volts to about 5 volts. Thus, if it is determined that the RF output signal that is applied to the headpiece 34 should have a peak-to-peak amplitude of about 3 volts, the supply voltage VA should be selected to be near 3 volts so that no unnecessary power is dissipated in the TX AMP 50.

Figure 9:
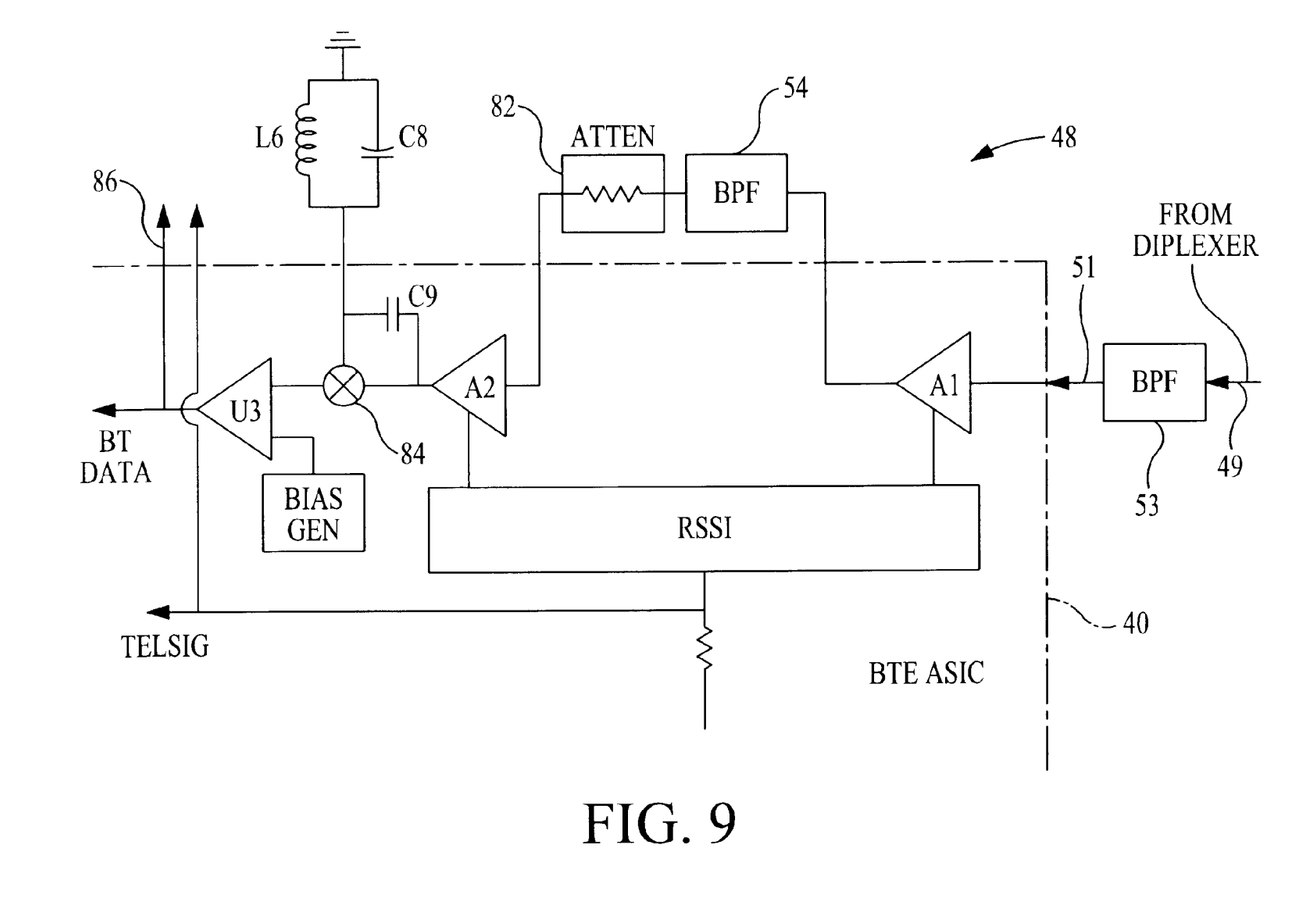
FIG. 9 illustrates a representative implementation of the frequency modulated receiver (FM RCVR) circuit of FIG. 3.

Turning next to FIG. 9, there is shown a preferred implementation of the frequency modulated receiver circuit (FM RCVR) 48 of FIG. 3. As indicated previously, use of the FM RCVR 48 is optional, as some embodiments of the BTE unit 20 may not use or require a backtelemetry signal.

When used, the FM RCVR 48 is used to receive and demodulate the FM backtelemetry signal transmitted from the ICS, or other remote device, to the BTE unit 32. The FM RCVR 48 is patterned after a conventional FM limiting IF amplifier and quadrature detector design, such as is found in the SE604, and the MC13156, commercially-available integrated circuits. Two external LC filters are used, one within BPF 54, and the other from L6 and C8, in order to achieve minimal component size, as well as to provide an external LC-resonator for the quadrature detector.

The FM RCVR 48 preferably operates from a 2 volt supply. The operating frequency should be something other than F1. In a preferred embodiment, the operating frequency is 10.7 MHz, with a bandwidth suitable for 100 KBaud data. An IF limiting amplifier A2 includes a received Signal Strength Indicator (RSSI) circuit which has an approximate dynamic range of 80 dB. The data format processed by the FM RCVR is FSK (frequency shift keying) with a frequency deviation of ±70 KHz. The output of data comparison circuit U3 is compatible with 2 V CMOS circuits. Its input sensitivity is approximately 20 $\mu$V. The input impedance is about 1.5 K$\Omega$.

The FM RCVR 48 shown in FIG. 9 includes four sub-circuit groups. In the preferred embodiment, the first sub-circuit group comprises a first IF amplifier A1. This first IF amplifier A1 comprises a fixed gain amplifier of, e.g., 39 dB, and has a 1.5 k$\Omega$ input impedance, and a 300 $\Omega$ output impedance. Its input range is from −90 dBm to −10 dBm. It's operating frequency is centered at 10.7 MHz, with a bandwidth of approximately 600 KHz. The two bandpass filters, BPF 53 and BPF 54, work to provide about 109 dB of rejection at the F1frequency, e.g., at 49 MHz. The first BPF filter 53 is a three-pole bandpass filter which rejects a large portion of the F1 transmitter signal. The DIPLEXER TX-to-RX isolation is about 30 dB. The second interstate BPF 54 is designed to provide a mid-band insertion loss of 12 dB. It is a combination of about 6 dB of mismatch loss, and 6 dB of attenuation provided by a resistive H-pad 82. Such a loss is necessary in order for the proper scaling of the RSSI amplifiers. A discrete LC-filter design was chosen for the BPF 54 in order to optimize component size and avoid the use of conventional ceramic filters. High selectivity is not needed, but good out-of-band rejection is needed to prevent transmitter bleed-through.

A second sub-circuit group is the IF limiting amplifier A2. It provides a selected gain, e.g., 55 dB of gain, with a limited output which compresses at −10 dBm. Its output is compatible with driving the quadrature detector and quadrature resonator. The RSSI circuit, which is coupled to the IF limiting amplifier A2, provides an output signal TEL SIG which is proportional to the received signal strength.

A third sub-circuit group within the FM RCVR 48 comprises a quadrature detector 84. Such quadrature detector 84 may be a doubly balanced 4-quadrant multiplier, as is known in the art. Its function is to demodulate the FM data.

A fourth sub-circuit group within the FM RCVR 48 comprises an output data comparator U3. The output data comparator U3 derives a threshold from the average level of the quadrature detector 84, and uses such threshold to define the demodulated data. An external pad connection 86 may be provided external to the ASIC 40 to facilitate connection of the output of comparator U3 with an appropriate filter capacitor.

In operation, the circuit described above in connection with FIGS. 3–9 operates at a power savings of about 70–90 mW over the conventional type of telemetry transmitter shown in FIGS. 1A and 1B. While 70–90 mW may not seem like a huge power savings, it represents a significant power savings when all factors (small size of the BTE unit, limited battery capacity, same ICS device, etc.) of the ICS system are considered.

As described above, it is thus seen that the present invention provides a compact, low power, highly efficient, RF telemetry transmitter circuit that may be used to transfer RF power from a limited power source, e.g., a small battery, through a barrier, such as the skin, to a device on the other side of the barrier, e.g., an implant device. It is further seen that such invention finds particular applicability for use within a behind-the-ear unit of a cochlear implant system.

As further described above, it is also seen that the invention provides a way to control the drive level of a fixed frequency RF carrier signal through pulse width modulation of a fixed frequency carrier input signal.

While the invention herein disclosed has been described by means of specific embodiments and applications thereof, numerous modifications and variations could be made thereto by those skilled in the art without departing from the scope of the invention set forth in the claims.

What is claimed is:

1. A cochlear implant system comprising an external part and an implant part, the implant part having an implantable receiver circuit and implantable means for generating and applying a stimulation current to a selected pair of implantable electrodes, the external part having an RF telemetry transmitter for transmitting power and data to the implant part, the RF telemetry transmitter comprising:

a fixed frequency oscillator that generates a fixed frequency clock signal;

a telemetry modulator circuit responsive to the fixed frequency clock signal and including a pulse width modulator for modulating the pulse width of the fixed frequency clock signal in accordance with a selected first modulation signal to produce an inter-stage drive signal; and a telemetry amplifier circuit responsive to the inter-stage drive signal that efficiently produces an RF output signal at the fixed frequency of the clock signal for transmitting to the implantable receiver circuit of the implant part; the telemetry amplifier circuit comprising:

a band pass filter circuit that rejects the higher harmonics of the inter-stage drive signal, while passing the fundamental frequency of the fixed frequency clock signal, thereby causing a drive level of the passed fixed frequency clock signal to vary as a function of the selected first modulation signal, and an output amplifier circuit that efficiently amplifies the inter-stage drive signal to produce an amplified fixed frequency output signal; and an antenna coil coupled to the telemetry amplifier circuit which receives the amplified fixed frequency output signal.

2. The cochlear implant system of claim 1 wherein the telemetry modulator circuit further includes means for modulating the fixed frequency clock signal in accordance with a second modulation signal, the second modulation signal comprising data that is to be transmitted to the implant part.

3. The cochlear implant system of claim 2 wherein the second modulation signal comprises an ON/OFF keying signal having a minimum ON time period and minimum OFF time period, and wherein at least n cycles of the fixed frequency clock signal are included within the minimum ON or minimum OFF time periods of the second modulation signal, wherein n is an integer of at least two, whereby a burst of at least n cycles of the fixed frequency clock signal appear in the fixed frequency clock signal when modulated by the second modulation signal.

4. The cochlear implant system of claim 2 wherein the second modulation signal comprises a frequency shift keyed signal (FSK) signal.

5. The cochlear implant system of claim 2 wherein the first modulation signal comprises a level select signal that may assume one of a plurality of values, each one of said plurality of values causing the fixed frequency clock signal to assume a respective pulse width.

6. The cochlear implant system of claim 5 wherein the first modulation signal comprises a level select signal that may assume one of four values, each one of said four values causing the fixed frequency clock signal to assume one of four possible pulse widths.

7. The cochlear implant system of claim 6 wherein each of the four possible pulse widths of the fixed frequency clock signal creates a fixed frequency clock signal having a duty cycle less than or equal to 50%.

8. The cochlear implant system of claim 1 wherein the output amplifier circuit of the telemetry amplifier circuit comprises a Class E amplifier.

9. The cochlear implant system of claim 8 wherein the Class E amplifier circuit includes a single transistor having a collector, a base, and an emitter, the bandpass filter circuit being coupled to the base of the single transistor.

10. The cochlear implant system of claim 9 further including a bias circuit coupled to the base of the single transistor, the bias circuit including means for generating a temperature compensated bias voltage to the base of the single transistor that, in the absence of a passed fixed frequency clock signal from the filter circuit, maintains the single transistor in an OFF state.

11. The cochlear implant system of claim 10 wherein an operating voltage, VA, is applied to the collector of the single transistor to provide collector modulation thereof, the emitter of the single transistor being connected to a ground potential, and wherein said operating voltage may assume one of a plurality of values.

12. The cochlear implant system of claim 1 wherein the telemetry modulator circuit comprises a circuit fabricated as part of an application specific integrated circuit (ASIC) used within the external part of the cochlear implant system, and wherein the telemetry amplifier circuit comprises a circuit fabricated from discrete components housed within the external part of the cochlear implant system.

13. The cochlear implant system of claim 12 wherein the oscillator circuit includes a discrete crystal connected to circuitry included within the ASIC used within the external part of the cochlear implant system.

14. The cochlear implant system of claim 13 wherein the oscillator circuit that generates the fixed frequency clock signal used by the telemetry modulation circuit also generates a second clock signal used for other purposes within the external part of the cochlear implant system.

15. The cochlear implant system of claim 12 wherein the ASIC further includes an FM receiver circuit for receiving a modulated backtelemetry signal from the implant part of the cochlear implant system.

16. The cochlear implant system of claim 1 wherein the fixed frequency clock signal has a fixed frequency that falls within the range of 40 to 60 MHz.

17. The cochlear implant system of claim 16 wherein the external part comprises a behind-the-ear (BTE) unit connected to a headpiece, and wherein the telemetry modulation circuit and telemetry amplifier comprise compact circuits housed within the BTE unit, and the antenna coil is housed within the headpiece.

18. A high frequency, highly-efficient, telemetry transmitter circuit for transmitting a modulated carrier signal to a remote receiver circuit, the telemetry transmitter circuit comprising:

a fixed frequency oscillator that generates a fixed frequency clock signal; and a telemetry modulator circuit responsive to the fixed frequency clock signal and including means for pulse width modulating the fixed frequency clock signal in accordance with a selected first modulation signal, the pulse width modulated fixed frequency clock signal comprising the modulated carrier signal.

19. The telemetry transmitter circuit of claim 18 further including a telemetry amplifier circuit that receives the pulse-width modulated (PWM) fixed frequency clock signal from the telemetry modulator circuit, the telemetry amplifier circuit comprising:

a band pass filter circuit that rejects the higher harmonics of the PWM fixed frequency clock signal, while passing the fundamental frequency of the fixed frequency clock signal, wherein a drive level of the passed fixed frequency clock signal varies as a function of the selected first modulation signal, and an output amplifier circuit that amplifies the passed fixed frequency clock signal to produce an amplified fixed frequency output signal, the amplified fixed frequency output signal comprising the modulated carrier signal;

antenna means coupled to the telemetry amplifier circuit for receiving the modulated carrier signal and transmitting it to the remote receiver.

20. A method for efficiently transmitting a modulated carrier signal to an implanted remote receiver, the method comprising:

generating a fixed frequency clock signal having a frequency of F1 MHz, the clock signal comprising a train of pulses, each pulse having a pulse width, W, with the time interval between the leading edge of the adjacent pulses comprising a fixed time period T1 seconds, where T1=/F1;

modulating the pulse width W of the first frequency clock signal in accordance with a selected first modulation signal to produce a pulse width modulated (PWM) inter-stage carrier signal, the first modulation signal defining the energy content, or drive level, of the PWM inter-stage carrier signal;

modulating the PWM inter-stage carrier signal with data in accordance with a selected second modulation signal to produce a dual modulated inter-stage carrier signal, the second modulation signal representing data to be carried to the remote receiver via the modulated carrier signal;

applying the dual modulated inter-stage carrier signal to a band pass filter circuit that rejects the higher harmonics of the fixed frequency clock signal, while passing the fundamental frequency of the fixed frequency clock signal, wherein the drive level of the passed fixed frequency clock signal varies as a function of the selected first modulation signal;

efficiently amplifying the passed fixed frequency clock signal to produce an amplified fixed frequency output signal to produce an RF output signal having a frequency of F1 MHz, the RF output signal having data embedded therein that varies as a function of the second modulation signal; and transmitting the RF output signal to the remote receiver circuit through an antenna coil.

* * * * *